United States Patent
Kamiya et al.

(10) Patent No.: US 6,432,142 B1
(45) Date of Patent: Aug. 13, 2002

(54) MOLD FOR UNIFORM PRESSING OF SUBSTRATE SIDE FACES, AND ARTIFICIAL BONE OF TITANIUM ALLOY HAVING HIGH BIOLOGICAL AFFINITY

(75) Inventors: Akira Kamiya; Akira Watazu; Katsuyoshi Naganuma; Jun Zhu, all of Aichi (JP)

(73) Assignee: Japan as represented by Secretary of Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/514,291

(22) Filed: Feb. 28, 2000

(30) Foreign Application Priority Data

Jul. 26, 1999 (JP) .......................................... 11-210338

(51) Int. Cl.[7] .................................................. A61F 2/36
(52) U.S. Cl. ................................ 623/23.53; 623/23.51; 623/23.54
(58) Field of Search ......................... 623/23.36, 23.5, 623/23.51, 23.52, 23.54, 23.53, 23.55, 23.57, 23.58, 23.59, 23.6

(56) References Cited

U.S. PATENT DOCUMENTS 6,124,015 A * 9/2000 Baker et al. ................. 428/100
6,180,033 B1 * 1/2001 Greshes ...................... 264/1.32
6,210,436 B1 * 4/2001 Weadock ..................... 424/422
6,221,111 B1 * 4/2001 Piveteau et al. ......... 623/23.57

OTHER PUBLICATIONS

T. Nonami, et al., "Hydroxyapatite Granule Implantation into Superplastic Titanium Alloy", Journal of the Ceramic Society of Japan, vol. 105 [8], pp. 710–712, 1997.

T. Nonami, et al., "Preparation of Hydroxyapatite–Granule––Implanted Superplastic Titanium–Alloy", Journal of Materials Science: Materials in Medicine, 9, pp. 203–206, 1998.

* cited by examiner

Primary Examiner—Corrine McDermott
Assistant Examiner—Hieu Phan
(74) Attorney, Agent, or Firm—Oblon, Spivak, McClelland, Maier & Neustadt, P.C.

(57) ABSTRACT

The invention relates to a mold having split dies to be arranged in opposition about a substrate and an outer frame situated about the perimeter of the split dies, wherein the outer frame and split dies function as a wedge and move slidably so as to convert the load produced by a vertical uniaxial press into load applied from two opposing directions across the horizontal, the split dies move in such a way as to compress the titanium or titanium alloy substrate and uniformly press the side faces thereof so as to impart the required configuration to the substrate, and to artificial bone having high biological affinity produced by the mold.

4 Claims, 3 Drawing Sheets

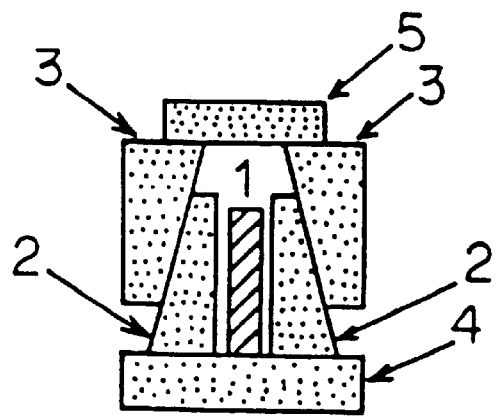
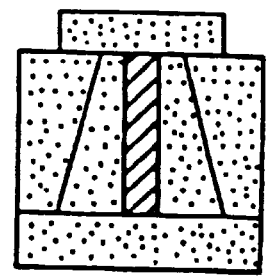
Before processing
After processing
FIG. 1A
FIG. 1B
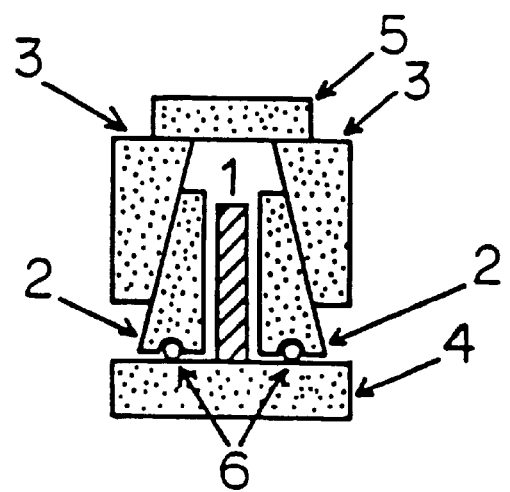
FIG. 2

Before processing

After processing

Before processing

After processing

MOLD FOR UNIFORM PRESSING OF SUBSTRATE SIDE FACES, AND ARTIFICIAL BONE OF TITANIUM ALLOY HAVING HIGH BIOLOGICAL AFFINITY

BACKGROUND OF THE INVENTION

1. Field of the Invention

The present invention relates to a technique for producing implants having high biological affinity by means of molding an artificial bone, such as an artificial hip joint stem, made of titanium or titanium alloy, through plastic working by using a split die in a high-temperature inert atmosphere, while simultaneously implanting granules of a bioactive ceramic, such as hydroxyapatite, into the surfaces thereof. More particularly, the invention relates to a mold for working a titanium or titanium alloy substrate into a desired product shape, and to artificial bone, such as an artificial hip joint stem, molded by hot pressing employing the mold.

2. Description of the Related Art

Medical implants, such as artificial tooth roots, artificial joints, and artificial bone, of various kinds made from titanium or titanium alloys exhibit both exceptional biocompatibility (i.e., the property to give rise to tissue no lesions, etc. in vivo) and mechanical properties, and are thus used increasingly. Recently, it has been attempted to produce an even better implant by imparting biological affinity (the ability to positively bond with bone in vivo) by implanting granules of a ceramic similar to a component of bone, such as hydroxyapatite, into the surface thereof (Japanese Laid-Open patent publication No. 5-57013/1993, "COMPOUND IMPLANT OF TITANIUM OR TITANIUM ALLOY AND MANUFACTURE THEREOF") using a casting method.

The cited invention is proposed as a substitute for surface coating formation by a conventional thermal spraying method. Specifically, surface coatings produced by the conventional thermal spraying method do not exhibit adequate bonding strength with metal, resulting in problems such as exfoliation of the coatings with extended use; therefore, granules of a bioactive ceramic are implanted into the surface of the implant, rather than forming a coating thereon. However, as titanium is highly reactive at high temperatures, when casting processes are employed, there forms a surface reaction layer that must be removed through grinding, etc. Accordingly, the bioactive ceramic granules employed in the cited invention have particle size of 1 mm or larger, which does not represent an appropriate particle size in terms of improving biological affinity thereof. Further, the problem of changes in product dimensions and shape due to grinding processes, etc., conducted after casting remains unsolved. With the foregoing in view, there has been developed a newer technique employing a superplastic forming process that is associated with minimal surface reaction layer formation, and that involves implanting granules of a bioactive ceramic, such as hydroxyapatite, into the surface of titanium or a titanium alloy ("Hydroxyapatite Granule Implantation into Superplastic Titanium Alloy", Tooru NONAMI, Katsuyoshi NAGANUMA, Akira KAMIYA, and Tetsuya KAMEYAMA, Journal of the Ceramic Society of Japan, Vol. 105, August ed., p. 710–712 (1997) and Japanese Patent Application No. 11-170436/1999, "IMPLANTS HAVING HIGH BIOLOGICAL AFFINITY AND A PRODUCTION PROCESS THEREFOR")

However, processes for implanting bioactive ceramic granules such as hydroxyapatite are either adapted for simple smooth surfaces, such as plate surfaces, or adapted primarily to small implants such as artificial tooth roots. Further technical efforts are needed to adapt such processes for use with other types of artificial bone, particularly artificial hip joint stems, etc., for which significantly increased demand is anticipated. Specifically, conventional techniques are not readily adapted to stems, etc. having long narrow forms that include various curves, and having larger dimensions than artificial tooth roots, etc.

Thus, in the technical field to which the invention pertains, there has been a need for development of a technique whereby granules of bioactive ceramic such as hydroxyapatite ranging from the micron order to the millimeter order can be uniformly implanted into the surface of artificial bone, such as an artificial hip joint stem.

SUMMARY OF THE INVENTION

The present invention provides a mold for pressing a substrate, as well as a titanium or titanium alloy artificial bone having biological affinity imparted to its surface, for use as an artificial hip joint stem, etc.

The invention relates to a mold comprising a split die to be arranged in opposition about a substrate, and an outer frame situated about the perimeter of the split die, wherein the outer frame and the split die function as a wedge and move slidably so as to convert the load produced by a vertical uniaxial press into load applied from two opposing directions across the horizontal, the split die move in such a way as to compress the titanium or titanium alloy substrate and uniformly press the side faces thereof so as to impart the required shape to the substrate; and to artificial bone having high biological affinity produced by imparting to a substrate the required shape through hot pressing using this mold, while simultaneously implanting granules of a bioactive ceramic, such as hydroxyapatite, into the surfaces thereof.

The invention is intended to solve the problems described previously, and has as an object to provide a mold for uniformly pressing the side faces of a substrate, which utilizes plastic deformation of titanium or titanium alloys at high temperature, making it possible to impart the required product shape thereto, while at the same time uniformly implanting granules of a bioactive ceramic, such as hydroxyapatite, into the surfaces thereof; and to provide titanium or titanium alloy artificial bone having high biological affinity obtained thereby.

To solve the problems described previously, the present invention comprises the following constitutions.

(1) A mold comprising split dies to be arranged in opposition about a substrate, and an outer frame situated about the perimeter thereof, wherein the outer frame and split dies function as a wedge and move slidably so as to convert the load produced by a vertical uniaxial press into load applied from two opposing directions across the horizontal, the split dies move in such a way as to compress the substrate and uniformly press the side faces thereof so as to impart the required configuration to the substrate.

(2) Titanium or titanium alloy artificial bone, which is produced by setting a titanium or titanium alloy substrate in the split dies of the mold as defined in (1) above, and then molding it through hot pressing.

(3) The artificial bone according to (2) above, having granules of a bioactive ceramic implanted in the surfaces of the substrate, which is produced by steps of spreading the granules of the bioactive ceramic over split die surfaces and/or substrate surfaces, and then implanting the granules of the bioactive ceramic present on the surfaces thereinto, while molding the substrate through hot pressing.

(4) The artificial bone according to (3) above, wherein the granules of the bioactive ceramic have particle size of from 30 to 100 μm.

Specifically, in a temperature region of from 700° C. to 900° C. in an atmosphere that is non-reactive with titanium, such as a vacuum or argon atmosphere, a pair of split dies of the desired product shape are arranged in opposition about a titanium or titanium alloy substrate, the split dies function as a wedge and move slidably within an outer frame so as to convert the load produced by a vertical uniaxial press into load applied from two opposing directions across the horizontal, thereby moving in such a way that the split dies compress the substrate during molding. In this case, since granules of a bioactive ceramic such as hydroxyapatite are spread over the split die surface and/or substrate surface, these granules are simultaneously implanted into the surface of the implant. That is, according to the present invention, molding of the material to its final product shape and imparting biological affinity thereto by implanting granules of a bioactive ceramic such as hydroxyapatite into the surfaces thereof can be accomplished simultaneously, and thereby a titanium or titanium alloy implant exhibiting exceptional biological affinity is produced.

In the present invention, titanium or a titanium alloy is used as the material for the substrate, specific examples thereof being inter alia JIS Type 2 pure titanium, Ti—6Al—4V alloy, Ti—4.5Al—3V—2Mo—2Fe alloy, Ti—6Al—7Nb alloy, Ti—5Al—2.5Fe alloy, Ti—13Nb—13Zr alloy, etc. Densified graphites, various types of machinable ceramics, various types of fine ceramics, etc. are used as the mold material.

The split dies are hollowed out to the desired product configuration. The granules of a bioactive ceramic such as hydroxyapatite are spread over the split dies surface or substrate surface by dispersing the granules within a suitable solution and applying them to the split dies surface or substrate surface by brush application, spraying, or dripping, or by dipping the split dies or substrate into a solution, withdrawing it, and then drying, or by some other process. As the aforementioned solution, preferably, polyvinyl alcohol aqueous solution, starch aqueous solution, gum arabic solution, vinyl acetate resin solution, acrylic resin varnish, collodion, water glass, and various other organic and inorganic solutions are used. Next, the substrate, which has been formed to approximate configuration by casting, machining, etc., is placed within the mold, set in a hot pressing apparatus similar to the hot press oven used in sintering of ceramics, etc., and subjected to hot pressing at from 700° C. to 900° C. in an atmosphere that is non-reactive with titanium, such as a 0.05 torr or less vacuum or argon, by slow pressing at a rate of 1 mm/min or less. As to the substrates having superplastic behavior, plastic deformation thereof begins at pressing load of 0 kg, with the pressing load gradually increasing, the mold contacts to the substrate closely. Accordingly, ideal pressing load and load time will depend on the material and configuration of the substrate to be formed. By means of the preceding process, the substrate is pressed to implant the granules of a bioactive ceramic such as hydroxyapatite into the surface thereof simultaneously.

The following detailed description of the invention concerns production of an artificial hip joint stem, but is merely illustrative and should not be construed as limiting of the invention. Production of the artificial hip joint stem employs a titanium or titanium alloy substrate like that indicated by 1 in FIG. 1, formed to approximate configuration by casting, machining, etc.

FIG. 1 depicts an example of a mold and substrate employed in application of the invention in production of an artificial hip joint stem. The entire assembly is set in a hot press oven adjustable to an atmosphere that is non-reactive with titanium, such as a vacuum or argon gas, and is subjected to pressing in a temperature range of from 700° C. to 900° C. at a pressing rate of 0.5 mm/min or less. The following detailed description refers to FIG. 1. Split dies 2, fabricated to correspond in shape to the desired stem, are assembled with substrate 1 accommodated therein. Through sliding movement of the die and an outer frame 3 via a taper thereof, pressing load in the vertical direction applied via an upper platen 5 is converted into horizontal load. As a result, split dies 2 move in such a way as to compress the substrate 1. Through initial provision of granules of a bioactive ceramic such as hydroxyapatite spread over the split die surfaces or substrate surfaces, the granules of a bioactive ceramic are implanted into the substrate surface during molding.

As the bioactive ceramic, preferably hydroxyapatite, tricalcium phosphate, carbonate apatite, or any of various other calcium phosphate salts, or any of various types of bioglass etc and used. Bioactive ceramic particle size is from 10 μm to 1 mm, and preferably from 30 μm to 100 μm.

To ensure smooth horizontal motion of the split dies, rollers 6 may be provided at the split die bases in the manner depicted in FIG. 2. In FIG. 2, a single roller is provided to each split die, but naturally a plurality of rollers could be provided where needed. Ball bearings, wheels, or the like is used in place of rollers where appropriate.

In the case of production of an artificial hip joint stem, an article having an artificial bone head of ceramic or the like pre-attached thereto may be used in processing. In such cases, the mold must be provided with a space for accommodating the head of the bone, as depicted in FIGS. 3 and 4. FIG. 3 depicts provision of this accommodating space to the upper platen, while FIG. 4 depicts provision thereof to the lower platen; in either design, the mold incorporates a member 7 for accommodating the head of the bone. Since in these cases the head of the bone can be fixed, a resultant advantage is that the stem axis can be correctly positioned with respect to the split dies.

While the preceding description of the invention concerns production of an artificial hip joint stem, the invention is not limited to application to artificial hip joint stems, having a wide potential range of application as a technique for the production of all manner of implants having high biological affinity for use as artificial shoulder joints, artificial elbow joints, artificial knee joints, artificial finger joints, and various other artificial joints, as well as a filler material for cranial bone, a filler material for mandibular bone, artificial vertebra, and various other types of artificial bone.

BRIEF DESCRIPTION OF THE DRAWINGS

FIG. 1 is an exemplary structural diagram (sectional) of a mold and substrate in accordance with the invention.

FIG. 2 is an exemplary structural diagram (sectional) of a mold and substrate in accordance with the invention.

Figure 3A:
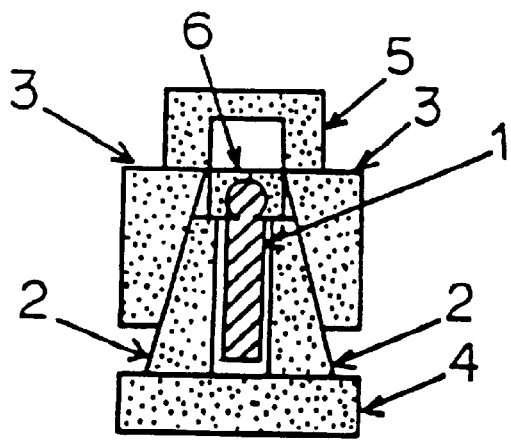
FIG. 3 is an exemplary structural diagram (sectional) of a mold and substrate in accordance with the invention.
Figure 3B:
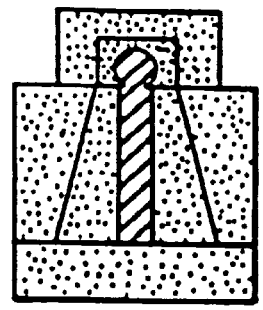
Figure 4A:
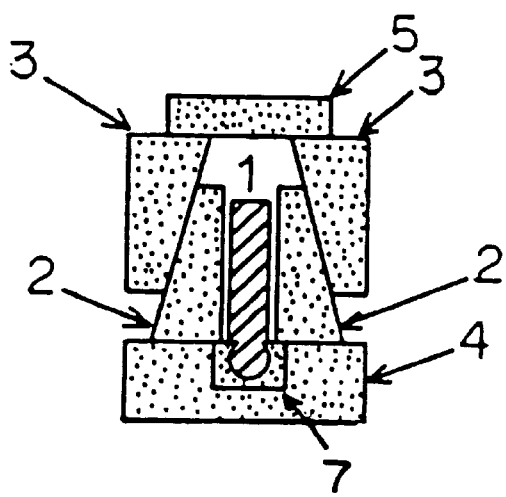
FIG. 4 is an exemplary structural diagram (sectional) of a mold and substrate in accordance with the invention.
Figure 4B:
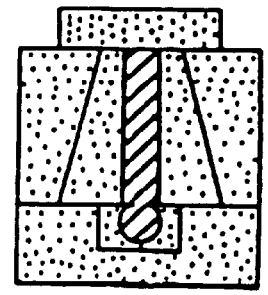
Figure 5:
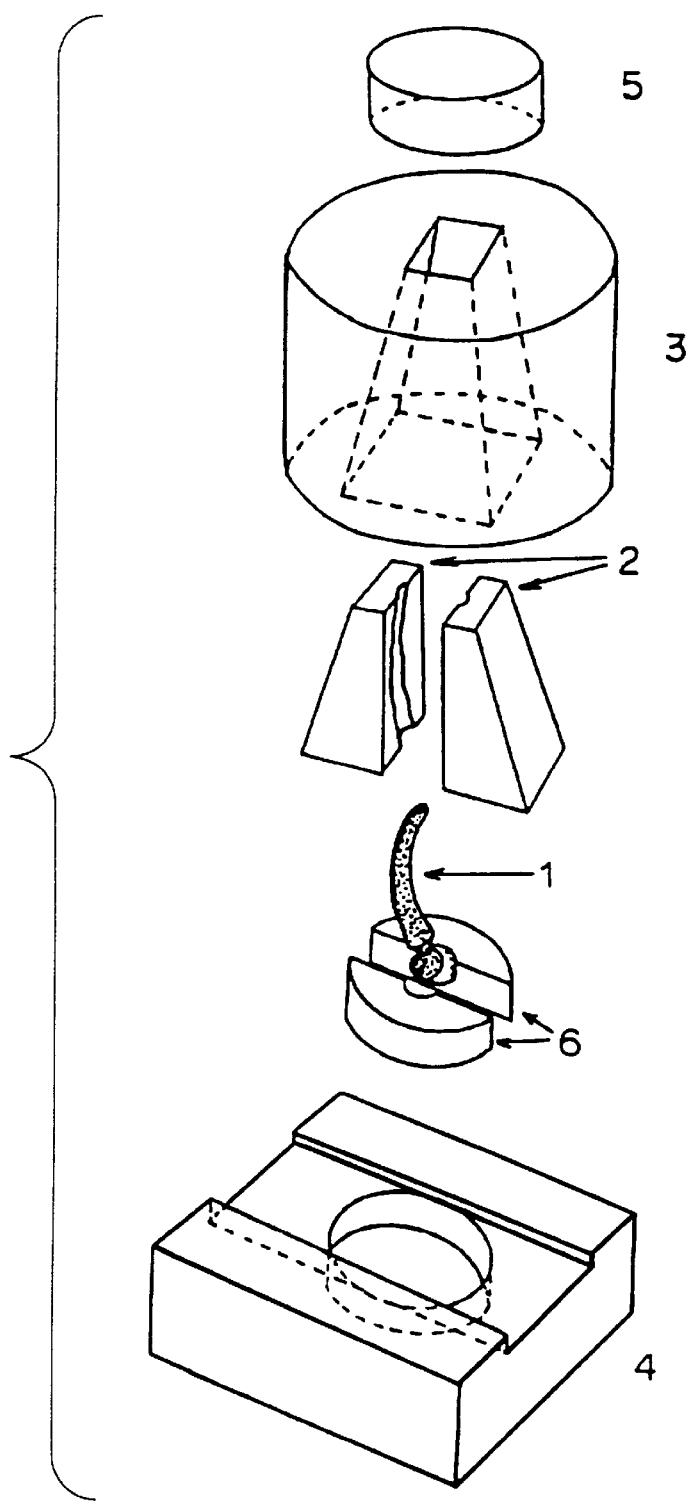
FIG. 5 is a structural diagram of a mold and substrate pertaining to an Example. In these FIGS., 1 is a substrate;
2 is a split die;
3 is an outer frame
4 is a lower platen.

5 is an upper platen; and 6 is a roller (FIG. 2) or 7 bone head accommodating member (FIGS. 3, 4, and 5).

DESCRIPTION OF THE PREFERRED EMBODIMENTS

The mold for uniform pressing of substrate side walls in accordance with the present invention as well as embodiments of titanium or titanium alloy artificial bone having high biological affinity produced therewith are now described with reference to the accompanying drawings. The following embodiments are merely preferrable examples of the invention and are not limiting of the invention.

EXAMPLE 1

A Ti—6Al—4V alloy was used to produce by a casting process a member having the configuration of a femoral component for a Charnley type artificial hip joint. The head of the bone was 22 mm in diameter and stem length was 120 mm. The surface of the member, having been ground subsequent to casting, was then coated with a dispersion containing 10 wt % hydroxyapatite granules average particle size 30 $\mu$m) dispersed in 0.2 wt % polyvinyl alcohol aqueous solution, and was then dried at room temperature. The resultant substrate (symbol "1" in FIG. 5) was assembled within a mold. FIG. 5 depicts an example of the system of FIG. 4 described in an aspect of the embodiment of the invention. The split dies are produced from a densified graphite material, hollowed out to final product configuration by means of electrical discharge machining, and washed thoroughly. Other parts of the mold were all fabricated of similar graphite material. The assembly was placed in a hot press oven and subjected to a pressing operation conducted in vacuo ($10^{-3}$ torr) at 850° C. with a deformation rate of 0.1 mm/min. When pressing load reached 150 kgf, this load level was maintained for a 20-minute period. The oven was then allowed to cool to ambient temperature, whereupon the substrate was unmolded. The hydroxyapatite powder was observed to be spread and implanted into the surfaces thereof. Thus, the artificial bone having high biological affinity, wherein the hydroxyapatite granules were implanted in the surfaces thereof, was produced.

EXAMPLE 2

A molding process was conducted analogously to Example 1, except that the temperature was 900° C. and pressing time was 10 minutes. Well-spread hydroxyapatite granules were observed to be implanted into the surfaces of the substrate. Thus, the artificial bone having high biological affinity, wherein the hydroxyapatite granules were implanted into the surfaces thereof.

EXAMPLE 3

A molding process was conducted analogously to Example 2, except that machinable ceramic (hexagonal system boron nitride) was used as the material for the split dies, with the split dies being hollowed out into final product configuration by a machining center. Well-spread hydroxyapatite granules were observed to be implanted into the surfaces of the substrate. Thus, the artificial bone having high biological affinity, wherein the hydroxyapatite granules were implanted into the surfaces thereof was produced.

EXAMPLE 4

A molding process was conducted analogously to Example 1, except that JIS type 2 pure titanium was used in place of Ti—6Al—4V alloy as the material for the substrate. Well-spread hydroxyapatite granules were observed to be implanted into the surfaces of the substrate. Thus, the artificial bone having high biological affinity, wherein the hydroxyapatite granules were implanted into the surfaces thereof was produced.

EXAMPLE 5

Using a Ti—4.5Al—3V—2Mo—2Fe superplastic alloy (SP— 700, manufactured by NKK) in place of Ti—6Al—4V alloy as the material, a member having the configuration of a femoral component for a Charnley type artificial hip joint was produced by a cutting process using a machining center. The head of the bone was 22 mm in diameter and stem length was 120 mm. Employed as the substrate 1 shown in FIG. 5, this was subjected to a molding process conducted analogously to Example 1, except that processing temperature was 750° C. and pressing load was 100 kfg. Well-spread hydroxyapatite granules were observed to be implanted into the surfaces of the substrate. Thus, the artificial bone having high biological affinity, wherein the hydroxyapatite granules were implanted into the surfaces thereof was produced.

EXAMPLE 6

A molding process was conducted analogously to Example 5, except that processing temperature was 700° C. and pressing time was 30 minutes. Well-spread hydroxyapatite granules were observed to be implanted into the surfaces of the substrate. Thus, the artificial bone having high biological affinity, wherein the hydroxyapatite granules were implanted into the surfaces thereof was produced.

EXAMPLE 7

A molding process was conducted analogously to Example 5, except that split dies fabricated of machinable ceramic (ROTEKKU TM, manufactured by Asahi Garasu) material and hollowed out to final product configuration using a machining center were used in place of the graphite split dies in Example 5. Well-spread hydroxyapatite granules were observed to be implanted into the surfaces of the substrate. Thus, the artificial bone having high biological affinity, wherein the hydroxyapatite granules were implanted into the surfaces thereof was produced.

Industrial Applicability

The present invention provides implants having high biological affinity of titanium or titanium alloy, wherein the granules of a bioactive ceramic such as hydroxyapatite were implanted into the surfaces thereof.

In particular, artificial hip joint stems produced by a process of the invention are of the cementless type and offer more secure interfacial bonding of titanium with bioactive ceramic such as hydroxyapatite, and hence exhibit superior performance in comparison of that produced by conventional methods, and therefore, a number of significant advantages in terms of medical instrument production techniques are afforded by this invention.

According to the present invention, a substrate is pressed to implant granules of a bioactive ceramic such as hydroxyapatite into the surface of the substrate simultaneously, and thereby implants of titanium or titanium alloy having high biological affinity, such as artificial hip joint stems are produced.

What is claimed is:

1. A mold comprising split dies to be arranged in opposition about a substrate, and an outer frame situated about the perimeter thereof, wherein the outer frame and split dies function as a wedge and move slidably so as to convert the load produced by a vertical uniaxial press into load applied from two opposing directions across the horizontal, the split dies move in such a way as to compress the substrate and uniformly press the side faces thereof so as to impart the required configuration to the substrate.

2. Titanium or titanium alloy artificial bone, which is produced by setting a titanium or titanium alloy substrate in the split dies of the mold as defined in claim 1, and then molding it through hot pressing.

3. The artificial bone according to claim 2, having granules of a bioactive ceramic implanted in the surfaces of the substrate, which is produced by steps of spreading the granules of the bioactive ceramic over split die surfaces and/or substrate surfaces, and then implanting the granules of the bioactive ceramic present on the surfaces thereinto, while molding the substrate through hot pressing.

4. The artificial bone according to claim 3, wherein the granules of the bioactive ceramic have particle size of from 30 to 100 $\mu$m.

* * * * *